US008507011B2

(12) United States Patent
Kross et al.

(10) Patent No.: US 8,507,011 B2
(45) Date of Patent: Aug. 13, 2013

(54) METHOD FOR SUPPRESSING OR PREVENTING FIBROUS ADHESION FORMATION USING A MULTICOMPONENT AQUEOUS OXYCHLORINE COMPOSITION PREPARED ON-SITE

(76) Inventors: Robert D. Kross, Bellmore, NY (US); Cleva Villanueva, Colonia Anahuac (MX)

( * ) Notice: Subject to any disclaimer, the term of this patent is extended or adjusted under 35 U.S.C. 154(b) by 233 days.

(21) Appl. No.: 12/727,725

(22) Filed: Mar. 19, 2010

(65) Prior Publication Data

US 2010/0330203 A1    Dec. 30, 2010

Related U.S. Application Data

(60) Provisional application No. 61/210,703, filed on Mar. 23, 2009.

(51) Int. Cl.
*A61K 33/14* (2006.01)
*A61K 33/20* (2006.01)
*A61L 2/00* (2006.01)
*A61L 2/18* (2006.01)

(52) U.S. Cl.
USPC ............. 424/661; 424/665; 422/28; 422/29; 422/37

(58) Field of Classification Search
USPC ........................ 424/661, 665; 422/28, 29, 37
See application file for complete search history.

(56) References Cited

U.S. PATENT DOCUMENTS

| | | | |
|---|---|---|---|
| 4,507,285 A | | 3/1985 | Kuhne |
| 5,622,725 A | * | 4/1997 | Kross ............................. 424/665 |
| 5,820,822 A | | 10/1998 | Kross |
| RE36,064 E | * | 1/1999 | Davidson et al. .............. 424/665 |
| 6,284,152 B1 | | 9/2001 | Kross |
| 2002/0001834 A1 | | 1/2002 | Keogh |
| 2007/0173755 A1 | | 6/2007 | Alimi et al. |

FOREIGN PATENT DOCUMENTS

| | | |
|---|---|---|
| EP | 1347754 A2 | 10/2003 |
| WO | 9802171 A1 | 1/1998 |

OTHER PUBLICATIONS

Chlorine Dioxide"In EPA Guidance Manual: Alternative Disinfectants and Oxidants," Apr. 1999, Chapter 4, pp. 4-1 through 4-41, accessed at www.epa.gov/ogwdw/mdpp/pdf/alter/chapt_4.pdf on Mar. 15, 2012.*
McGraw-Hill Encyclopedia of Science & Technology, 9th edition, McGraw-Hill: New York, 2002, pp. 303.*
MacMillan Encyclopedia of Physics, vol. 4, Simon & Schuster: London, 1996, pp. 1677.*
Dynamic, Absolute, Kinematic Viscosity accessed online at www.engineeringtoolbox.com/dynamic-absolute-kinematic-viscosity-d_412.html on Apr. 11, 2011.*
Ansel et al., Pharmaceutical Dosage Forms and Drug Delivery Systems, Lippincott Williams & Wilkins: New York, 1999, pp. 88 (Table 3.3).*
Namazi, Hamid, et al., Novel Use of Botulinum Toxin to Ameliorate Arthrofibrosis: An Experimental Study in Rabbits. Toxicologic Pathology. 2007, vol. 35, pp. 715-718.
Buckenmaier, C.C. et al., Comparison of antiadhesive treatments using an objective rat model. Am Surg 1999; 65:274-282.
Reed, et al,. A neurokinin 1 receptor antagonist decreases postoperative peritoneal adhesion formation and increases peritoneal fibrinolytic activity Proc. Nat'l Acad. Sci. vol. 101,No. 24, 9115-9120, Jun. 15, 2004.
Reed, et al., Neurokinin-1 Receptor and Substance P Messenger RNA Levels lincrease during Intraabdominal Adhesion Formation. Journal of Surgical Research 108, 165-172 (2002).
Kenyon, A.J et al., "Controlled wound repair in guinea pigs, using antimicrobials that alter fibroplasia" in Am J Vet Res. 47(1):96-101 (1986).
Gordon, Gilbert et al., The Chemistry of Chlorine Dioxide, Prog. Inorg. Chem. 15:201, pp. 234-286, (1972).
Gordon, Gilbert and Emmenegger, Complex Ion Formation between ClO2 and ClO2-, Inorg. Nucl. Chem. Letter vol. 2, 1966, Pergamon Press Ltd. (1966).
Masschelein, W. J., Chlorine Dioxide; Chemistry and Environmental Impact of Oxychlorine Compounds. p. 57, Ann Arbor Science publishers, (1979).
Körtvélyesi, Zsolt, "Analytical Methods for the Measurement of Chlorine Dioxide and Related Oxychlorine Species in Aqueous Solution" thesis for Doctor of Philosophy, Miami University, Chemistry, 2004.
Schier, F. Tetrachlorodecaoxide does not jeopardize anastomotic healing: an experimental study in animals, Ped. Surg. Intnl, (17), No. 2-3, pp. 180-184, Mar. 2001.
Robson, M.C. et al., Hypochlorous Acid as a Potential Wound Care Agent, Part II; J. Burns and Wounds, vol. 6, p. 80-90, (2007).
Dakin's solution. (2010). In Encyclopedia Britannica. Retrieved Aug. 19, 2010, from Encyclopaedia Britannica Online: www.britannica.com/EBchecked/topic/150035/Dakins-solution.

(Continued)

*Primary Examiner* — James H. Alstrum-Acevedo
(74) *Attorney, Agent, or Firm* — Henry D. Coleman; R. Neil Sudol

(57) ABSTRACT

A composition and method are described for suppressing or preventing fibrous adhesion formation using a multicomponent aqueous oxychlorine composition. Fibrous adhesions typically form during healing of tissue, for example following a surgical procedure. A multicomponent oxychlorine composition is provided for irrigating the tissue which minimizes post-surgical adhesion formation, the composition containing both chlorine dioxide and chlorite ion, and a complexion thereof. The chlorine dioxide level generally is in an effective range of $ClO_2$ concentration from about 10 ppm to a maximum of about 110 ppm. In a preferred embodiment, a physiological composition is provided in a thickened form to increase retention in the area being treated. The composition is preferably based on a standard saline solution converted to the oxychlorine composition just prior to use by sequential addition of aqueous concentrates of a chlorite salt, a hypochlorite salt combined with a physiological buffer-producing salt of a multibasic acid, and an acidifying agent, optionally including a thickening agent.

31 Claims, 1 Drawing Sheet

(56) References Cited

OTHER PUBLICATIONS

Tuma B, Aron M, Frota R, Desal MM, Kaouk J, Gill IS. Feasibility of laparoscopic partial nephrectomy after previous ipsilateral renal procedures. Urology 2008; 72:584-588.

Cooper RG, Mitchell WS, Illingworth KJ, et al., The role of epidural fibrosis and defective fibrinolysis in the persistence of postlaminectomy back pain. Spine 1991; 16:1044-48.

Kulkarni AV, Massie JB, Zauner F, Murphy M, Akeson WH. Novel biomechanical quantification methodology for lumbar intraforaminal spinal nerve adhesion in laminectomy in disc injury rat model. J Neurosci Methods 2007; 166:20-23.

Sabuncuoglu H, Bavbek M, Sabuncuoglu B, Gadelha E, Kase K, Preul M. Attenuation of postlaminectomy epidural fibrosis with monoclonal antibodies against intercellular adhesion molecule—1 and CD-18. Spine J 2007;7:459-465.

Ward, B. C., and Panitch, A. Abdominal Adhesions: Current and Novel Therapies. J Surg Res, 2009, in press. [doi:10.1016/j.jss.2009.09.015].

Al-Musawi, D. and J. N. Thompson; Adhesion prevention: state of the art. Gynaecological Endoscopy, 2001 10. 123-130.

diZerega, G.S. et al.,; A randomized, controlled pilot study of the safety and efficacy of 4% icodextrin solution in the reduction of adhesions following laparoscopic gynaecological surgery. Human Reproduction, vol. 17, No. 4. pp. 1031-1038,2002.

Tang, Choong-Leong et al.; A Randomized Controlled Trial of 0.5% Ferric Hyaluronate Gel (Intergel) in the Prevention of Adhesions Following Abdominal Surgery. Annals of Surgery, vol. 243, No. 4, pp. 449-455, Apr. 2006.

Thornton, Melvin H. et al., Clinical evaluation of 0.5% ferric hyaluronate adhesion prevention gel for the reduction of adhesions following peritoneal cavity surgery: open-label pilot study; Human Reproduction, vol. 13, No. 6, pp. 1480-1485, 1998.

Verco, Shelagh J.S. et al.; Development of a novel glucose polymer solution (icodextrin) for adhesion prevention; pre-clinical studies. Human Reproduction, vol.15, No. 8, pp. 1764-1772, 2000.

Parcells, Jeremy P., M.D. et al., Using antimicrobial solution for irrigation in appendicitis to lower surgical site infection rates. The American Journal of Surgery (2009) 198, 875-880.

Ruiz -Tovar, Jaime et al.; Effect of Peritoneal Lavage with Clindamycin-Gentamycin Solution on Infections after Elective Colorectal Cancer Surgery. J American College of Surgeons, vol. 214, No. 2, Feb. 2012, pp. 202-207.

Chen, Y. and Hills, B.A.; Surgical Adhesions: evidence for absorption of surfactant to peritoneal mesothelium. Aust N Z J Surg. Jun. 2000;70(6):443-7.

Fact Sheet on the Federal Register Notice for Stage 1 Disinfectants and Disinfection Byproducts Rule; EPA 815-F-98-010; Dec. 1998; http://water.epa.gov/lawsregs/rulesregs/sdwa/stage1/factsheet.cfm.

PH of a Sodium carbonate solution?; Yahoo! Answers; http://answers.yahoo.com/question/index?qid=20080123194841AAuebco, printed Aug. 27, 2012.

Tripotassium phosphate; http://www.fao.org/ag/agn/jecfa-additives/specs/Monograph1/Additive-480.pdf, Published in NMRS 55B (1976).

* cited by examiner

METHOD FOR SUPPRESSING OR PREVENTING FIBROUS ADHESION FORMATION USING A MULTICOMPONENT AQUEOUS OXYCHLORINE COMPOSITION PREPARED ON-SITE

CROSS REFERENCE TO RELATED APPLICATIONS

This application claims priority in U.S. Provisional Patent Application No. 61/210,703 filed Mar. 23, 2009, the entire contents of which are incorporated by reference herein.

TECHNICAL FIELD

This invention relates generally to the preparation of oxychlorine formulations for medical and antiseptic application, especially related to adhesion reduction resulting from surgical intervention, and the preparation of the formulation on site just prior to administration, to preserve effectiveness.

BACKGROUND OF THE INVENTION

Injury to internal tissue during surgery is followed by a healing process that frequently results in the attachment of adjacent tissues and organs by a fibrous mass, commonly referred to as adhesions. In essence it is a fibrous bridge that blocks the movement between two or more tissues that normally move freely, causing attendant pain. Post-surgical adhesions often occur following pelvic, abdominal and thoracic surgery, although there are many sites in the body where they occur from non-surgical intervention as well. Data have suggested that 67% to 93% of patients will develop adhesions following non-gynecologic abdominal surgery and 55% to 100% of patients will develop adhesions following gynecologic surgery. Despite refinement in operative technique and the recent introduction of products intended to minimize adhesion formation, the problem of postoperative adhesions remains a major cause of pain; and infertility after gynecologic surgery. Many of those patients who develop adhesions after gynecologic surgery may not experience any pain or discomfort from them, but it is impossible to predict which ones will have such problems, so it is important to minimize or eliminate adhesion problems in all such surgery.

All surgeons must deal with both the potential for adhesion formation after surgery, as well as the sequelae of adhesions from previous surgeries, which may markedly increase the difficulty of any particular surgical case. In addition to pelvic pain, abnormalities of bowel function, and small bowel obstruction can occur as a result of adhesions. Consider just gynecologic surgery, as a representative example. De novo or new adhesions may form at a site where none existed before, but where a surgical procedure was performed. Examples include a myomectomy incision for uterine fibroids or an ovarian incision at the time of ovarian cystectomy. De novo adhesions may also develop away from the site of surgery, such as adhesions developing around the tubes and ovaries at the time of a cesarean section. Adhesions may also reform following adhesiolysis or adhesiectomy.

Three general types of adhesions exist—filmy, vascular, and cohesive. The underlying pathology of all three, however, is similar. It is helpful to use the formation of peritoneal adhesions as the basis for understanding the underlying mechanism of the present invention, irrespective of where it is applied. The peritoneum is composed of multiple layers. The mesothelium is the innermost layer, a layer of connective tissue which contains the blood vessels, and a basement membrane. When the peritoneum (or other part of the body, including the skin) is injured (inevitable during surgery), there is an inflammatory response.

During the initial phase of this inflammatory response, inflammatory mediators and histamine are released from mast cells and leukocytes. Capillaries located within the connective tissue dilate and an increased permeability of the capillary wall is noted. This allows leukocytes, red blood cells and platelets to become concentrated at the site of in injury. A fibrinous exudate is thus formed at the site of injury. Multiple factors such as prostaglandins, lymphokines, bradykinin, serotonin, transforming growth factor and other chemotactic agents are present within the exudate material. It is generally understood that many of these factors trigger the activation of fibroblasts, the cells responsible for collagen, the fibrous protein which comprises the scaffold of adhesions. Without the replication of these fibroblasts, triggered by this inflammatory response, the production of collagen would not take place.

Before proceeding further, it is valuable to list additional areas where adhesions develop, whether from surgery or other aberrant physiological conditions. These include, among others:

Pleural adhesions from repeated thoracotomy to control the spread of cancer;
Pleural adhesions due to pulmonary tuberculosis;
Renal adhesions after renal surgery;
Pericardial adhesion following by-pass surgery;
Fallopian tube adhesions which develop after infection (e.g., genital tuberculosis);
Peritoneal adhesions associated with tuberculosis;
Peridural fibrosis following lumbar surgery (e.g., laminectomy);
Symblepharon (eyelid adhesions) from ocular burns, conjunctival infections (e.g., Chlamydia), Stevens-Johnson syndrome (allergic reaction to drugs e.g., bactrim);
Peritoneal adhesions resulting from radiotherapy to treat abdominal cavity cancer (e.g., colon, cervical, endometrial).

When surgery is involved, there are four general approaches to adhesion reduction. These may generally be described as 1) minimizing injury during surgery, 2) reducing the local and inflammatory response, 3) inhibiting the coagulation cascade and promoting fibrinolysis, and 4) using barriers for separation of surfaces at high risk for adhesion formation. Regarding category 1) it is generally acknowledged that, even with the best techniques, the very nature of surgery involves the destruction of cells and the triggering of the inflammatory cascade. The Category 3) approach involves biochemical processes, quite different from both Categories 2) and 4). In Category 3) there are continuing, though not yet productive, efforts to interrupt and/or control the complex series of proteolytic events associated with activated platelets, their release of mediators that promote vesicle formation and platelet adherence, which then lead to enzyme activation, thrombin generation and associated fibrin formation. Before dealing with Category 2), which is the focus of this inventive disclosure, it is appropriate to make brief mention of the Category 4) approach, and its success. It should be noted, though, that use of physical barriers to suppress adhesion formation may be considered for only several of the circumstances listed above, where fibrous adhesions develop.

The barrier approach: To separate the surgically-incised tissue from adjacent tissues, by wrapping or coating the affected organ (generally) with a material that prevents contact of the fibrinous exudate from the injured tissue with adjacent tissues with which it might develop connective adhesions. There are limited areas where this approach has been effective, but such use has its attendant dangers as well. For example, Seprafilm® Adhesion Barrier is indicated for the reduction of post-surgical adhesions in patients undergoing abdominal or pelvic laparotomy. The type and frequency of adverse events reported are consistent with events typically seen following surgery when used as directed. Seprafilm should not be wrapped around an intestinal anastomosis as such usage may result in increased anastomotic leak-related events. Also achieving some success, in certain areas, have been Polyactive™, PRECLUDE Peritoneal Membrane™, Tissucol™ and INTERCEED(TC7)™. These are of a variety of compositions; for example, Seprafilm is a chemically modified sodium hyaluronate/carboxymethylcellulose fabric that is crosslinked with zinc, and is bioresorbable. INTERCEED(TC7) is a fabric composed of oxidized, regenerated cellulose that is also absorbed after a certain time period. PRECLUDE is a unique configuration of expanded polytetrafluoroethylene (ePTFE), Tissucol is a fibrin glue, and Polyactive is a degradable barrier, composed of a poly(ethyleneglycol) and poly(butyleneterephthalate) copolymer. All of these require manual placement in confined areas, with a significant level of dexterity, and all these physical systems have limitations in terms of where they may be used in the body, as well as demonstrating varying levels of success.

A more efficient way of contacting all the incised/eroded/ or compromised tissues would be with a liquid infusion, where some component(s) of such infusion would have the capacity to interfere with the normal biochemical processes which otherwise result in the development of fibrous adhesions. A few such infusing solutions have been suggested: Ringer's lactate has been reported as effective, but a body of research indicates otherwise. Interperitoneal infusion studies of Lipiodol (an iodinated poppy seed oil) and methylene blue have been carried out in rats, and although "significant differences" in adhesion suppression were found between Lipiodol and control animals, none were found between methylene blue and control, nor between Lipiodol and methylene blue. The latter can be interpreted as indicating that the significance in the difference between Lipiodol and control was not that large, although mathematically still statistically valid.

The possibility of another type of liquid infusion with the potential for reducing the tendency for fibroblast replication arose from a publication by Kenyon et al., "Controlled wound repair in guinea pigs, using antimicrobials that alter fibroplasia" in Am J Vet Res. 1986 Jan; 47 (1):96-101. The publication is the result of work sponsored by one of the inventors (Kross) who at the time was the Director of Research at the Alcide Corp., a developer of oxychlorine (oxidizing) germicides. The latter were based on chlorous acid compositions which had, as one of its degradation products, the gaseous compound "Chlorine Dioxide" [$ClO_2$].

A gelled chlorous acid composition was applied to a full-thickness incision in a rabbit's skin, which had been previous infected with a pathogenic organism. In addition to determining that there was full destruction of the infecting organism, it was noticed that the healed skin surface ". . . had a reduced level of scar formation. Microscopic evaluations indicated greatly reduced inflammatory infiltrates in Alcide—(i.e., chlorous acid)-treated wounds, indicating lack of fibroblast-stimulating activity by monocytes." In reference to the Kenyon article, as noted in U.S. Pat. No. 5,622,725 (Kross), "irrigation of wounds with combined lactic acid and chlorite solutions significantly . . . promotes healing and epithelization by minimizing collagenous scar formation" (col. 11, lines 44-47). The present inventor continued to investigate these systems, and found that while the chlorous acid may have played a major role in that reduction, the acidity of the system was too low (e.g., pH≈3) to be physiologically compatible, particularly with internal tissues, and it was later learned that there are a number of stronger oxidants present, though transiently, in the chlorous acid degradation pathway to form $ClO_2$, which are of significantly greater oxidative capacity (e.g., $Cl_2O_2$, HOCl, $Cl_2$). It should be noted that the $ClO_2$ that formed represented no more than about 5 to 10% of the end products of the chlorous acid disproportionation.

Continued investigation suggested, though, that $ClO_2$ may itself have some beneficial properties at physiologically compatible pHs, and perhaps combine its known antimicrobial activity in wound environments with the possibility of minimizing adhesion and scar formation. This possibility was discussed in the '725 patent, which was primarily directed to the use of $ClO_2$ in treating or preventing infections associated with peritoneal dialysis (specifically so-called Continuous Ambulatory Peritoneal Dialysis [CAPD]). The '725 patent describes using >125 to about 1000 ppm of $ClO_2$ as a component of a peritoneal dialysis fluid, or in an aqueous solution for infusion into a peritoneal cavity wound in order to disinfect the wound and promote healing. No examples were provided which would support the contention that $ClO_2$, per se is efficacious in minimizing or preventing fibrous adhesion formation. The evidence for the potential to minimize eventual adhesion formation was simply inferred from a series of comparative studies involving cell cultures of isolated polymorphonuclear leukocytes, "which are among the first cells to be found at a wound . . . " (col. 13, line 54), with regard "to their response to a $ClO_2$ solution." The comparative agent was the known anti-inflammatory Ibuprofen.

The $ClO_2$ in the treatment solution taught in the '725 patent was required to be present such that the "molar ratio of chlorine dioxide to any residual chlorite in the composition is at least 5:1 . . . " (see claim 1, column 16, lines 8-10). In fact "(t)he chlorine dioxide solutions . . . have a relative molar ratio of chlorine dioxide to residual chlorite of at least 5:1, typically at least 7.5:1, and preferably at least 10:1." (Col. 4, I. 31-34). Chlorite, according to the '725 patent, is to be minimized in the treatment solutions because of its detrimental effects. (See Col. 5, I. 48, 49: ". . . defined chlorine dioxide-to-chlorite molar ratios that limit tissue irritation . . . ", and Col. 8, I. 46-50: ". . . in order to utilize the germ-killing and non-inflammatory qualities of chlorine dioxide, it is preferable to isolate it from chlorites . . . (which have detrimental cytotoxic effects)."

$ClO_2$ generation, according to the '725 patent, was accomplished in either of three ways. All three involved the spontaneous degradation of chlorous acid ($HClO_2$) by a so-called disproportionation mechanism. One technique involved the use of a strong acid combined with chlorite to form high levels of $HClO_2$, which immediately degrades to $ClO_2$ and several Cl-containing anions. The second involved the use of a moderate-strength acid, plus a triggering material such as chloride ion or certain sugars, leading to a lower yield of $ClO_2$. The third technique involved contact of chlorite with heat-activated sugars, at an acidic pH, whereby $ClO_2$ is formed in high levels. The '725 patent requires a minimum of 125 ppm of $ClO_2$ to be effective in these peritoneal treatment applications, to a maximum concentration of 1000 ppm.

The present invention is the result of investigations to determine whether $ClO_2$ solutions can indeed significantly suppress, or even prevent, the formation of fibrous adhesions in actual surgical procedures, in contrast to the suggested ability to lower the tendency for such activity by cell culture methods. There were no specific details, methods nor Examples provided in the '725 patent to validate this theoretical projection which was based on isolated cell cultures. It should be stressed that reduced scar [collagen] formation had only been observed by Kenyon et al. when freshly incised wounds to the skin had been treated with a chlorous acid composition, of which $ClO_2$ was generated at a low percentage range (believed to be $\geqq 0.01$-$0.02\%$).

However the present inventors were successful in demonstrating effective suppression of post-surgical adhesions in actual mammalian surgeries, by employing actually lower concentrations of mixed oxychlorine compositions, combining both $ClO_2$ and chlorite ions, where the $ClO_2$ itself was present at levels below 125 ppm; and the chlorite ion actually played a role in the activity. They also were successful in demonstrating that $ClO_2$ in combination with hypochlorite and/or hypochlorous acid could be similarly effective at $ClO_2$ levels below 125 ppm. Thereafter the inventors developed practical methods of optimizing the effects so as to bring such technology into operating theaters, and related environments.

It should be noted that in the '725 patent, the stipulated molar ratio of chlorine dioxide to chlorite ion, $ClO_2:ClO_2^-$, was 5:1 at a minimum concentration of 125 ppm for the $ClO_2$. This was dictated by the need for the solution to be non-irritating, as chlorite ion can be a tissue irritant at significant levels, while also being effective in the presence of significant organic matter, such as in the peritoneal cavity, in catheter biofilms, and in the dialysis fluids used for the CAPD treatment. $ClO_2$, being an oxidant, is susceptible to reductive loss by reaction with many organic materials, particularly dextrose, which is the major solute in CAPD solutions. Our studies have shown that $ClO_2:ClO_2^-$ ratios of $\geqq 5:1$ are not only unnecessary, but contraindicated by the probable need for chlorite ion to enhance activity, as will be explained below. In addition, a level of $ClO_2$ of 125 ppm, the lower level for the range claimed in the '725 patent [125 to 1000 ppm], represents the approximate maximum $ClO_2$ concentration needed for $ClO_2$ in the multicomponent oxychlorine system of the present invention to be effective in suppressing adhesions.

$ClO_2$ is a gas that has a number of properties which militate against its usage at higher levels. One of these negative properties is $ClO_2$'s high inhalation toxicity. OSHA, the Occupational Safety and Health Administration of the US Department of Labor, allows only a 0.1 ppm $ClO_2$ maximum level (i.e., 0.28 mg/m$^3$) in the air of workers exposed to it for 8 hours, on a daily basis. Tied to this is the fact that $ClO_2$ is a highly diffusive gas, and can permeate through virtually any plastic container in which it is contained. The higher the level in solution, the greater is the potential for diffusion to the surrounding air, and the concomitant potential for negatively affecting the respiratory capacity of both medical personnel and, more critically, the medically-compromised patients in the environment. For comparison, the corresponding allowable OSHA air maximum for chlorine (a noxious gas) is ten-times greater than for $ClO_2$, namely 1 ppm. For short term contact of aqueous solutions of $ClO_2$ with respect to surgical sites, the concern is less for the tissue involved than the quantities that could get into the air during application of a $ClO_2$ solution, to reach and adversely affect the human lung.

There are three supplemental structures that are believed to play a role in the inventive method, and contribute to the activity of the multicomponent oxychlorine composition taught herein.

Role of Chlorite Ion

First is the reported existence of a $Cl_2O_4^-$ complex anion, comprised of one molecule of $ClO_2$ and one of $ClO_2^-$. This is a bimolecular association complex $[ClO_2.ClO_2^-]^-$, which according to Masschelein, is an association complex that forms in neutral aqueous solution $[ClO_2.ClO_2^-]^-$. This $(Cl_2O_4)^-$ complex is also mentioned in Kuhne, U.S. Pat. No. 4,507,285, and Kross (U.S. Pat. No. 6,284,152): "The basis for the stability of the $ClO_2$ in the presence of $ClO_2$ ion appears to derive from the reported existence of a bimolecular charge-transfer complex involving one molecule each of $ClO_2$ and $ClO_2^-$, as follows:

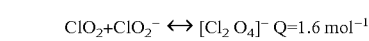

Thus, in solutions that contain both $ClO_2$ and $ClO_2^-$, it can be expected that a portion of the $ClO_2$ will be tied up in complex form, and not be available per se as free $ClO_2$. It should be also noted that the oxidation potential of $[Cl_2O_4]^-$ is reportedly higher than that of $ClO_2$, so that $ClO_2$ solutions also containing $ClO_2^-$, and therefore the complex ion, would be expected to have a greater oxidation capacity than might be expected from simply that calculated from the level of $ClO_2$ present. This increased capacity would be expected to be associated with, for example, greater disinfection or a greater ability to destroy oral malodorants than a comparable $ClO_2$ solution with no additional chlorite present." (See also Kross U.S. Pat. No. 5,820,822). The existence of this oxidizing complex, pairing a non-ionized chlorine dioxide molecule and a chlorite ion, when together in neutral solution, was initially established in publications by Gordon et al., in 1966 and 1972. The present inventors postulate that the basis for this complex formation arises from the fact that the chlorine dioxide molecule is an electron-deficient free radical, and can readily accept the excess electron of the chlorite ion into its molecular orbital, creating a stable dimer, with a more diffuse negative charge.

Second is that the chlorite ion itself is a component of another product, with known antiadhesion properties. Studies on a compound called Tetrachlorodecaoxide (TCDO), which is a negatively charge chlorite-containing drug of chlorine and oxygen [Schier, et al.,], found that "it displays antiadhesive properties when applied intra-abdominally."

Role of Hypochlorite

Third, hypochlorite, the oxychlorine ion $ClO^-$, can play a contributing role in the multicomponent aqueous oxychlorine formulations of the invention, depending upon the manner (i.e., ratio) in which the reactive components are combined. Hypochorite formulations have an historic role, and have been used as an antimicrobial solution since the days of World War 1 under the name Dakin's solution or the Carrel-Dakin method of wound treatments. This solution is a highly diluted antiseptic, consisting of a buffered sodium hypochlorite solution (0.4% to 0.5%). It has been used to prevent and treat skin and tissue infections that could result from cuts, scrapes and pressure sores. It has also been used before and after surgery to prevent surgical wound infections. Ordinary household hypochlorite (aka "bleach") is sold at concentrations of typically, from 5.25% to about 6.50%. It can be particularly noted here that hypochlorous acid, at a 0.01% concentration, showed promise as an effective antimicrobial wound irrigant, associated with improved wound closure (Robson et al., 2007).

The inventive method and composition was the result of the consideration the above factors, wherein the potential contribution of the chlorite ion for enhanced activity of chlorine dioxide ($ClO_2$)-containing compositions, could play a role in the oxidative inactivation of those factors which would otherwise trigger fibroplasia. Since chlorite has been shown to enhance the activity of $ClO_2$-containing systems, [i.e., the $Cl_2O_4^-$ complex with $ClO_2$] and in combination with other oxidants [e.g., TCDO], the inventors focused on $ClO_2$-containing compositions where chlorite was present in significant levels relative to that of $ClO_2$. The '725 patent states that the $ClO_2/ClO_2^-$ molar ratio must be $\geq 5:1$, and the level of $ClO_2$ must be greater than 125 ppm (to about 1000 ppm) for treating and preventing microbial infections in the peritoneal cavity, and promoting healing. The potential inhalation toxicity of such elevated levels, and the difficulty in preparing such high-concentration $ClO_2$ compositions further motivated the present inventors to explore other options at lower levels of $ClO_2$, through inclusion of significant levels of chlorite ion to enhance its activity.

$ClO_2$-Containing Compositions; Necessity for on-site Preparation

It is well known that $ClO_2$ is a rapidly diffusive gas, and readily lost to the environment. It cannot be stored in most common containers, and in the compressed gas form will readily explode. Compositions containing $ClO_2$ must therefore be prepared on-site, directly before use. When $ClO_2$ is dissolved in aqueous solvents, the higher the concentration of $ClO_2$ in the solution the higher could be the diffusive loss to the surrounding air, and the greater the potential inhalation hazard to users of such products. The elevated levels of $ClO_2$ taught in the '725 patent would be predisposed to such problems.

The inventive method and composition was directed to a simplified, easily practicable technique for preparing $ClO_2$-containing compositions directly on-site, for immediate use by medical practitioners. The following description of the inventive method and composition has resulted from due consideration of these additional factors, and demonstrates the success of this in-depth exploration, including the successful application of this new technology to compositions resulting in a marked reduction of post-surgical adhesions following mammalian surgeries.

SUMMARY OF THE INVENTION

It is an object of this invention to provide an in situ method for the preparation of multicomponent oxychlorine solutions for lavage of surgical intervention sites, particularly directed to the disruption of the biochemical processes which ordinarily result in fibrous adhesion formation.

It is a further object of this invention to formulate such multicomponent oxychlorine solutions by oxidation of a chlorite salt to chlorine dioxide, wherein there is sufficient residual chlorite ion, after such oxidation, to allow for the existence of, and participation by a chlorine dioxide-chlorite complex anion species in such solution.

It is an additional object of this invention to provide an in situ method for the preparation of multicomponent oxychiorine solutions for lavage of surgical intervention sites, wherein the multicomponent oxychiorine solutions are comprised of chlorine dioxide and unconsumed hypochlorite, remaining from oxidation of chlorite to chlorine dioxide, such that the activity of these solutions can be directed to both site antisepsis as well as the disruption of biochemical processes which otherwise result in fibrous adhesion formation. These solutions would accordingly contain minimum residual chlorite ion.

These and other objects are accomplished by the present invention, which provides both methods for the convenient in situ preparation of the multicomponent oxychlorine compounds for irrigation of surgical intervention sites to minimize, inhibit or reduce the likelihood of post-surgical adhesion formation upon surgical-site closure, in due course, and/or antisepsis of the surgical incision site during, and following closure.

These and other objects are accomplished by the invention, which provides methods for using the mixed oxychiorine compositions for a variety of pathological treatments, generally but not exclusively those involving surgical interventions.

In one preferred embodiment, the method is directed to an application of a multicomponent aqueous oxychiorine formulation for the minimization, inhibition and/or prevention/reduction in the likelihood of post-surgical adhesions in a broad range of surgical sites throughout the mammalian body. The mixed oxychlorine solutions that can be used cover the range from those containing both chlorine dioxide and chlorite ion, and presumably the complex ion comprised thereof which absorbs the chlorite electrons into the more diffuse molecular orbital of the $Cl_2O_4^-$ anion, to those combining chlorine dioxide and unreacted hypochlorite, which may or may not favor disinfection over adhesion diminution. The chlorine dioxide level in the mixed solution of either type, will generally lie in an effective range of $ClO_2$ concentrations from about 10 ppm to a maximum of about 110 ppm. In a preferred embodiment, a physiological saline solution containing the $ClO_2$ can be prepared in thickened, i.e., viscous form, which leads to a greater retention time of the treatment fluid in the area being treated, either intra-corporeally or topically. In such case the standard salines must be prethickened prior to addition of the active components. While the focus in this disclosure is on the use of the inventive method and solutions prepared therefrom for invasive surgical applications, these solutions would lend themselves as well to topical sites. These would include surface wounds which penetrate the skin to the underlying fibroblast layer, to thereby inhibit, minimize scar formation, as well as to such other sites as optic pathologies and ocular infections and prevention/reduction in the likelihood thereof if such areas may have been exposed to detrimental pathogens. The inventive compositions, of course, could be applied to surface surgical sites to provide topical antisepsis before, during and after skin closure.

The inventive method is based on the incorporation of a chlorite-containing salt in isotonic saline, concomitant with or followed by the incorporation of a hypochlorite salt and a buffer-producing salt. The resulting solution is then selectively acidified to reduce the pH of the medium to a range where the hypochlorous acid counterpart of the hypochlorite ion will form, resulting in oxidation to a chlorine dioxide ($ClO_2$)-containing oxychlorine mixture, and the acid then added will react with the buffer-producing salt to form a physiologically compatible buffer. The nature of, and the concentrations of the various components are carefully selected so that there will be:

either an excess of chlorite ion or hypochlorite in the resulting mixture;

a level of initial chlorite salt to produce a level of $ClO_2$ in the desired concentration range for the treatment solution;

a dibasic or tribasic acidifying agent employed, of appropriate acid strengths (i.e., of multiple $pK_a$ values), to both a)—acidify the oxychlorine composition so as to optimize the conversion of the chlorite salt to $ClO_2$ and minimize alternative reactive pathways leading to unwanted chlorine-containing anions, and b)—create a pH and tonicity in the final treatment solution that is in a physiologically-acceptable range.

optionally, a physiologically-compatible thickening agent, should a treatment solution of increased viscosity be desired that is stable in the presence of the oxidizing systems introduced into, and created by, the oxychlorine treatment system.

The chlorite salt is preferentially sodium chlorite, although any other alkali- or alkaline-earth salt would be usable. The salt of the oxidant-forming species must be a hypochlorite salt, whether an alkali- or an alkaline-earth salt, because of the role of the hypochlorite species in this method. A number of di- or trivalent salts, such as, but not limited to, a carbonate, phosphate or borate may be utilized as the alkaline counterpart of a buffering salt that would form upon acidification of the oxychlorine-charged saline.

When a thickened formulation is preferred, there are a number of thickening agents, of both natural and synthetic origin, that may be employed. One advantage of the method is that the resulting formulations are all high-level disinfectants, so that any microbial contamination associated with the thickener, or even having been introduced as an artifact of the solution preparation, will be rapidly destroyed.

The inventive method takes advantage of the universal presence of sterile saline containers in medical institutions and surgical operatories, as the base for creation of these solutions, and readily lends to the ease of such preparation directly on site. As discussed below, the conversion of the contents of such physiological saline solutions to the treatment solution requires only a few minutes, at most. The basis for the transformation of sterile saline into the treatment solution requires the simple, and/or sequential addition to the saline container of 1)—an aqueous solution of a chlorite salt, 2)—an aqueous solution of a salt of an oxidant combined with a salt of a buffer-producing salt when acidified, and thereafter 3)—an aqueous solution of an acid to reduce the pH of the medium to a pH below about 7 sufficient to convert the oxidant salt to its corresponding acid form capable of oxidizing chlorite to chlorine dioxide. In a preferred embodiment, the oxidant salt is sodium hypochlorite, the buffer-producing salt is sodium carbonate, and said acid is citric acid.

The sequential procedure for preparing the treatment solution is best carried out by introduction of the activating solution concentrates into the sterile saline container through the use of hypodermic syringes and needles. The needles are inserted through the septa of the saline container, either the bottle or usual plastic container which holds the saline. The volumes of concentrates injected are determined by the volume of the saline solution (e.g., 500 ml or 1-liter), the desired level of $ClO_2$ in the treatment solution, a determination of whether a 2-step or 3-step injection technique is preferred, and whether the resulting treatment solution should be one where the oxychlorine composition should be a combination of chlorine dioxide and chlorite (and inferentially the additional formation of the $Cl_2O_4^-$ complex ion therefrom), or whether a composition comprised of $ClO_2$ and hypochorite) ($OCl^-$) is desired. The choice may depend on the primary intended purpose of the treatment solution.

Further characteristics of the invention are summarized as follows:

a)—$ClO_2$-containing solutions which include at least one other oxychlorine species are demonstrably effective in suppressing the formation of fibrous adhesions which appear primarily following surgical intervention, where injured cells, in the classic inflammatory response, release a cascade of fibroblast growth stimulating factors. By extension, this invention should apply to dermal injuries which penetrate to the fibroblast layer, such as inhibition, prevention or reduction of the likelihood of formation and/or correction of keloids, as well as to physiological sites which are prone to adhesion formation although direct surface disruption are not the stimulating factor e.g., eyelid adhesions from conjunctival infections.

b)—The molar ratio of chlorine dioxide to chlorite ion [$ClO_2$:$ClO_2^-$] effective in disrupting fibrous adhesion formation, unless when hypochlorite is the second intended oxychlorine species, is significantly less than the minimum in the '725 patent of $\geq 5:1$. In fact, it is generally lower than about a 3.5:1 ratio, with no concern about the potential tissue irritation effects from the residual chlorite in the treatment solutions. The chlorite is believed to be a necessary component to facilitate the creation of the active dimeric complex $Cl_2O_4^-$ anion.

c)—The maximum concentration of $ClO_2$ in the oxychlorine treatment solutions is below 125 ppm, that is about 110 ppm, and lower concentrations are demonstrably effective. Those lower concentrations limit the potential irritation from residual chlorite ion levels, which are concomitantly lower.

Simple procedures are used to provide safe and rapid production of the treatment solutions directly in an operating theater, or wherever such solutions are required. The solutions can be produced "as needed," utilizing materials already present in those facilities. The preparation of the $ClO_2$ is by a different, more efficient system, than that taught by Kross '725, which relied on the acidification of a chlorite salt to chlorous acid, which then undergoes a series of breakdown reactions where "at most", and under the most ideal conditions involving high acidity, the reaction will have a maximum theoretical yield of $ClO_2$ of 80%:

$$5HClO_2 \rightarrow 4ClO_2 + HCl + 2H_2O \text{ (4ClO}_2 \text{ from 5HClO}_2\text{), [80\% yield]}$$

although a more common reaction, and more likely in the Kross teachings, is much less efficient:

$$4HClO_2 \rightarrow Cl^- + 2ClO_2 + ClO_3^- + 2H^+ + H_2O \text{ (2ClO}_2 \text{ from 4HClO}_2\text{), [50\% yield]}$$

In this more common "disproportionation" reaction, although much of the chlorite is destroyed, a significant portion is transformed to the chlorate ion ($ClO_3^-$) which has a known toxicity.

Conversely in the present invention, the conversion can approach a stoichiometric yield, being based on the reaction of hypochlorous acid [HOCl] and chlorite [$ClO_2^-$] wherein one HOCl molecule will directly react with two molecules of chlorite, in mildly acid solution, to provide an amount of $ClO_2$ equal to that of the initial chlorite [$ClO_2^-$], as shown in the following equation:

$$HOCl + 2ClO_2^- \rightarrow 2ClO_2 + Cl^- + OH^-$$

The criticality of maintaining the pH of the solution in which the oxidation takes place will be shown later. Should the pH fall much below about pH=4, even in localized areas during acidification, that there will be a conversion of HOCl to $Cl_2$, the reaction of this with chlorite leads to undesired chlorine-containing anions, thereby diluting the efficacy of the oxidation to $ClO_2$.

In a preferred embodiment, in order to achieve desired levels of $ClO_2$ rapidly, it is appropriate to start with an excess of chlorite ion added to the aqueous medium, and thereafter or concomitantly introduce the required level of hypochlorite ion (as the salt) plus a buffer-producing salt. Then the alkaline system is acidified appropriately (based on acid, its concentration, and rate of addition), which then converts hypochlorite ion to hypochlorous acid, to achieve the predetermined yield of $ClO_2$. That preferred means of achieving the desired $ClO_2$ level, through control of the hypochlorite addition, results in a residual level of unreacted chlorite ion. That is the reason that the ultimate ratio of $ClO_2$ to $ClO_2^-$ in the treatment solutions is significantly less than that taught by the Kross '725 patent. However, to prepare a mixed oxychlorine treatment solution, which has a greater focus on antisepsis, while still maintaining the ability to markedly reduce adhesion formation, such a solution should be comprised of $ClO_2$ and hypochlorite/hypochlorous acid [$OCl^- \leftarrow\rightarrow HOCl^-$], with the balance determined by solution pH, with all the initial chlorite oxidized to $ClO_2$. This solution has no potential to form the $Cl_2O_4^-$ complex anion, among its active oxychlorine mix.

To practice this invention, i.e., to prepare the $ClO_2$ treatment solutions in a manner most conducive to use by the medical practitioner, an efficient way has been developed by which the solutions can prepared directly before use, and thereby avoid the diffusive losses that $ClO_2$ gas is subject to. The solutions are prepared in a salt solution that is compatible with mammalian tissues; i.e., one that is isotonic with the fluids in the tissues (where 0.9% sodium chloride, or saline is the common solution employed). As indicated above, such solutions are universally available in medically-oriented facilities in pouches and/or bottles as "sterile saline." A preferred method for adapting these solutions for direct preparation of the inventive treatment solutions involves a choice of two or three steps, as follows (where the components of the solutions in the first two steps may be combined into one, as disclosed in subsequent text):

1. Introduction (e.g., injection) of an aqueous chlorite concentrate into the sterile saline container (which can be the standard half-liter plastic pouch, or a bottle, or other container);

2. Introduction (e.g., injection) of an alkaline hypochlorite concentrate into the sterile saline container, where the concentrate also contains a buffering-producing monohydrogen salt upon acidification (e.g., sodium carbonate or sodium phosphate) at such a concentration that the subsequently acidified chlorite/saline solution attains the desired level of $ClO_2$ in a solution, with a pH which is compatible with biological tissue (preferably from about 5.5 to about 8.0).

3. Introduction (e.g., injection) of an aqueous acid concentrate into the sterile saline container (which acidifies the chlorite/hypochlorite/buffer-producing salt/saline solution to an appropriate degree for the subsequent oxidation of the chlorite ion to chlorine dioxide). The relative levels of chlorite and hypochlorite will determine if the final oxychlorine system is one based on $ClO_2$ and $ClO_2^-$, or $ClO_2$ and $OCl^-/HOCl$.

The final solution can then be used in a manner where sterile saline might otherwise be used, say as an irrigant during surgical procedures. The solution will have the dual benefit of both disinfecting the area, because of the powerful germicidal effects of $ClO_2$, and presumed contribution of the chlorine dioxide-chlorite complex, as well as an agent to abort the triggering action of fibroblast stimulating factors associated with the inflammatory response of damaged tissues.

DETAILED DESCRIPTION OF THE INVENTION

Figure 1:
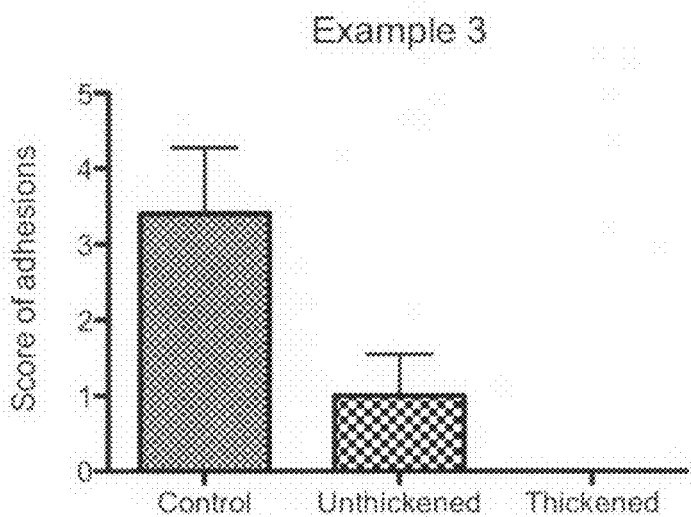
FIG. 1 is a bar graph of adhesion severity scores in Example 3 for thickened and unthickened $ClO_2$ oxychlorine-saline solutions and control saline solution.

This invention is based upon the discovery of a method to produce multicomponent aqueous oxychlorine-containing mammalian treatment solutions, wherein there are at least two such active species are present in the solutions, which solutions are of benefit in reducing the adverse effects of surgical interventions and for a variety of topical pathological applications. One of the oxychlorine components is chlorine dioxide ($ClO_2$).

The method lends itself to a very rapid and convenient preparation of these chlorine dioxide-containing aqueous systems directly on site of the medically-oriented application, where the resulting solution is automatically created as a sterile isotonic composition, at a physiologically-compatible pH. The implicit benefit of this method is that $ClO_2$ is a gaseous material which, though highly soluble in water, can rapidly dissipate by diffusion through the walls of most plastic containers, such as are in use for virtually all aqueous fluids used in medical environments. Ordinarily $ClO_2$, which cannot be stored in gaseous form, must be prepared in advance from concentrates, and then suitably diluted for use in intended compositions. The inventive method provides for virtually instantaneous creation of $ClO_2$-containing oxychlorine compositions, where oxychlorine species other than $ClO_2$ can play an active role in the beneficial application of these systems to a variety of pathological conditions.

The basis of this inventive method is the sequential introduction/injection of several solution concentrates into commonly available isotonic sterile saline solutions available in medical (including dental) facilities and operatories. The concentrates are those of a chlorite salt, a hypochlorite salt+buffer-producing salt, and an acidifying agent. The reaction of these components is based on the oxidation of the chlorite, by hypochlorous acid, to $ClO_2$. The chlorite salt concentrate may be conveniently combined with the hypochlorite/buffer-making salt in a single solution, in a preferred embodiment. After injection of the oxychlorine components, singly or in two steps, the acidifying agent is then introduced.

The concentrations of the various aqueous solutions are selected such that a desired level of $ClO_2$ in the treatment solution is achieved, and the nature and level of the additional oxychlorine component of the treatment solution are determined by the relative molar ratios of initial chlorite and hypochlorite concentrations in the injected solutions. Both the nature and the rate of addition of the acidifying agent play a role in achieving the eventual composition of the treatment solution. There are two options in this preparation, one is to use less hypochlorite, mole wise, than the chlorite, so that an excess of chlorite ion remains. The other is to use a higher molar amount of hypochlorite, vis-á-vis the chlorite, creating an excess of hypochlorite and/or hypochlorous acid in the treatment solution, in addition to the $ClO_2$. The non-specific referral to hypochlorite and/or hypochlorous acid in the treatment solution arises from the fact that at pH 6.0, hypochlorite is 100% present in the hypochlorous acid form. At pH 7.4 it is 100% present as hypochlorite ion. Both pHs lie in the physiologically-compatible range. There appear to be inherent benefits of both chlorite or hypochlorite predominating compositions, depending on their intended mammalian applications.

It is important to understand the various factors that must be considered in use of hypochlorite to oxidize the chlorite ion [ClO$_2$] to chlorine dioxide [ClO$_2$] in this inventive method, in order to obtain the optimum composition, through the conversion of [ClO$_2^-$] to [ClO$_2$]. These factors include:

1)—The chlorite ion in the isolated concentrate must initially be present in the physiological saline, at a pH of >>7.4, and preferably >pH 9, if introduced separately prior to the addition of the hypochlorite ion and the sodium carbonate species. If combined with the hypochlorite and buffer-producing salt, the pH should be >11. The alkaline pHs will ensure stability of the chlorite ion. 2)—Following addition of the hypochlorite/buffer-forming salt to the chlorite/saline mixture, the chlorite ion must be present at a molar ratio, with respect to the hypochlorite ion, of greater than 2:1, so that unreacted chlorite ion remains in the final composition, if that composition is desired to be one that would facilitate to creation of the Cl$_2$O$_4^-$ complex anion.

3)—The acidification of the solution should be carried out in such manner, with the selected acidifying agent, such that the pH of the system does not fall below about 3.5, except transiently, in order to a)—prevent significant conversion of the hypochlorous acid (that is formed from the hypochlorite ion) to Cl$_2$, and b)—the conversion of the chlorite ion to chlorous acid which occurs to a significant degree below pH 3.5 (at that pH, only about 2% of chlorite ion transforms to the corresponding chlorous acid form, i.e., HClO$_2$. 4)—The acidification of the solution should involve a moderately strong acid [such as an α-hydroxy acid, capable of forming an appropriate buffer in an acceptable physiological range] such that the pH of the alkaline system containing the chlorite and the carbonate, which form the eventual buffer drops rapidly to below a pH of about 7, to minimize any side reactions of the chlorite to form undesired chlorine-based anions, specifically chlorate and chloride. Following are two brief summaries of:

1)—the relevant reactions involving chlorite species with hypochlorous acid and chlorine, and
2)—the equilibrium characteristics of these hypochlorite/hypochlorous acid/chlorine species in aqueous solutions at varying pH values.

Chlorite Reactions with Hypochlorous Acid/Chlorine Species

The following four reactions provide insight into the invention taught herein. They are in a sequence from higher to lower pH systems, and provide the Gibbs Free Energy [ΔF°] of each reaction.

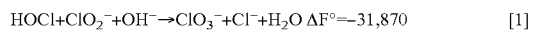   [1]

   [2]

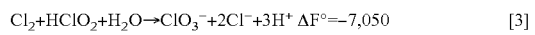   [3]

   [4]

These reactions can be interpreted to mean that reaction [1] operates most effectively in an alkaline environment, because it requires the presence of OH$^-$ ions, in which medium it will produce significant levels of chlorate and chloride ions. It is important to establish conditions which minimize the participation of this reaction, by keeping the level of OH$^-$ ion as low as possible. As will be seen in the following chart, at pH values of about ~7.4 and below, the relative amount of OCl$^-$ is de minimus, having converted to HOCl and the level of OH$^-$ as required by equation [1] is decreasingly less. It is therefore important that the pH of the alkaline solution be rapidly reduced to below about pH 6 to minimize chlorate formation. Although the ΔF° of the reaction [1] is the largest negative value, it can be disfavored in systems with low OH$^-$ concentrations, where a rapidly acidified solution will quickly reduce the pH to below about ~6. It is important, when acidifying, that the liquid be actively mixed, to avoid local concentrations of high acidity.

Reaction [2] is the primary focus of this Method's teaching, where the hypochlorite ion having converted to hypochlorous acid reacts with chlorite stoichiometrically, 1 mole of HOCl to form two moles of ClO$_2$, and the chlorine atom in the hypochlorite moiety is reduced to chloride ion. Note in the table below that HOCl converts to Cl$_2$ at greater acidities. Thus [2] is the reaction that is favored for the optimum chlorite conversion to ClO$_2$, and it again should be mentioned that the additional presence of chlorite ion is favored for the optimum activity of the inventive Method [to be later explained]. The ΔF° of reaction [2] is still quite high (as compared with [3] and [4]), and that is the favored driving energy force of this Method.

The table below illustrates that as the pH of these systems fall below 4, hypochlorous acid converts rapidly to Cl$_2$, with a lower energy driving force for that reaction; a reaction that favors chlorate and chloride ion formation. The ΔF° of reaction [3] is about ¼ of the higher pH reactions, and it is of benefit in the inventive method to suppress the creation of lower pH systems in order to minimize any side reactions leading to chlorate and chlorite ion formation. And in even lower pH systems, where reaction [4] holds sway, the concentration of acid in the system is such that there is sufficient HClO$_2$ for two such entities to be available for the reaction. However the acidity of such solutions has to approximately or preferably be below the value of the pK$_a$ of chlorous acid (~1.9), at which pH only half of the chlorite exists as chlorous acid.

The experience of one of these inventors [Kross] is that strong chlorous acid solutions alone, in the absence of oxidizing chlorine, will disproportionate (i.e., change to a mixture of more stable species, while preserving the total electronic balance of the reaction products) to form, at most, a maximum of 80% chlorine dioxide, although closer to, or less than 50% is more often attained. Such disproportionation reactions as follows can occur, all of which are less efficient means of converting chlorite to chlorine dioxide in acidic environments: e.g., 80% yield, high acid conditions: 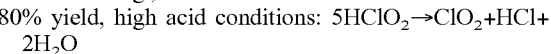

50% yield, moderate acid: 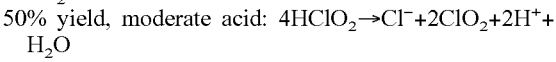

This is why it is important to use the acidification step of the chlorite/hypochlorite formulation as the final step in the inventive method. Otherwise the yield of ClO$_2$ will be less than optimum.

Chlorine Species

Chlorine in water can be present as the dissolved gas (Cl$_2$), and/or as hypochlorous acid (HOCl), and/or as hypochlorite ion (OCl$^-$). The three forms of chlorine can exist together in equilibrium, where their relative proportions are determined by the pH value and temperature.

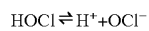

As evident in the tabulation below, between a pH of about 2.1 to about 7.1, the predominant form of chlorine is HOCl.

| The Effect of pH on the distribution of Chlorine species in water at 25° C. | | | |
|---|---|---|---|
| pH | $Cl_2$ | HOCl | $OCl^-$ |
| 2 | 52% | 48% | 0% |
| 3 | 18% | 82% | 0% |
| 4 | 0% | 100% | 0% |
| 5 | 0% | 100% | 0% |
| 6 | 0% | 100% | 0% |
| 7 | 0% | 70% | 30% |
| 7.4 | 0% | 0% | 100% |
| 7.4 and up | 0% | 0% | 100% |

In this instant Method, the optimum conditions for oxidation of the chlorite ion by hypochlorous acid exist at pHs from about 4 to about 6.5.

To illustrate the above approach as applied for the suppression of post-surgical adhesion formation, but by no means to be limited by this illustration, using a three-step sequential process, 1)—injection of 1 ml of a chlorite solution in purified water adjusted to a pH of ≧11 into the port or septum of a bag and/or bottle of sterile saline;

2)—injection of 5 ml of an aqueous solution of appropriate levels of sodium hypochlorite (NaOCl) and sodium carbonate ($Na_2CO_3$) into the container, followed by;

3)—injection of 5-ml of an aqueous solution containing an amount of citric acid solution appropriate to lower the pH of the solution (from the buffer-forming salt) to an acidic pH range sufficient to convert the hypochlorite to hypochlorous acid, and achieve the physiologically-compatible final isotonic solution.

The solutions in 1), 2) and 3) would be serially injected through the septum of the container, followed by mild agitation (e.g., alternate squeezing and/or shaking of the bag) after each injection. The solution at the end of this operation would appear yellow, from the $ClO_2$ formed, with the solution at the predetermined desired pH, and the pH of the solution lying in the range of about ~6.5±0.7. As the HOCl formed, from the hypochlorite in the acidified saline, and then reacted with the buffer-producing salt [e.g., sodium carbonate ($Na_2CO_3$)], the excess acidity would convert the mixture to a buffered (e.g., bicarbonate system ($NaHCO_3$) at a physiologically acceptable pH. The $ClO_2$-containing saline solution, whether with additional chlorite or hypochlorite ion, as required, would then be used to perfuse the contents of the incised body cavity, to suppress adhesion formation with concomitant antisepsis, or applied to the body to treat some other pathological condition (e.g., a topical wound, or as an ophthalmic irrigant to treat a pathological condition of the eye), to serve additionally as an effective antiseptic.

Experience with these solutions thus far suggests that an effective range of $ClO_2$ concentrations for these systems extends from about 10 ppm to a maximum of about 110 ppm. The relative molar amount of chlorite ion, with respect to the $ClO_2$ would range from about 0.25 to about 1.0. The initial concentration of chlorite ion, as a final percent introduced into the physiological saline (from a suitable concentrate, considering the degree of dilution into the saline) would range from about 20 mg/liter to about 200 mg/liter (ppm), expressed as the chlorite ion. Using the preferred salt thereof, sodium chlorite, this would correspond to about 26.8 to about 268 mg/liter of the salt, on the pure basis. For those circumstances where the oxidation of chlorite to $ClO_2$ by hypochlorite (as hypochlorous acid) results in residual chlorite ion in the finished oxychlorine composition, the corresponding amount of sodium hypochlorite would range from about 6 mg/liter (6 ppm) to 60 mg/liter (60 ppm) range.

When it is desired that the final oxychlorine composition be comprised of both $ClO_2$ and hypochlorite/hypochlorous acid, the same approximate levels of chlorite ion would apply, but the corresponding amount of sodium hypochlorite would be larger than specified above. In the latter case, it is appropriate to use an amount of sodium hypochlorite that is in a molar excess to that of the chlorite used, that ranges from about a 10% to about a 50% molar excess with respect to that of the chlorite level. In practical terms, for a 10 ppm yield of $ClO_2$, the range of appropriate NaOCl concentrations would be equivalent to from about 18 mg/liter to about 25 mg/liter. At the upper end of the range of $ClO_2$ in the desired multicomponent oxychlorine formulation, i.e., of about 110 ppm of $ClO_2$, the NaOCl concentration range would lie in the about 180 mg/liter to about 245 mg/liter concentration range. Those skilled in the art of oxychlorine chemistry, employing a matrix approach to optimize the mixed oxychlorine composition for their designated application, should be readily capable of establishing the appropriate concentrations of reactants in order to achieve their preferred formulation.

The amount of acidifying agent to be used in these oxychlorine compositions will be dependent upon the acid selected. A mono-, di- or tribasic acid is generally appropriate, of a moderate acid strength, and one that has a $pK_a$ that lies in the range of about 3.8 to about 7.1 would be considered for such use. Consideration should also be given to the nature and qualities of the buffer-producing alkaline salt, used in combination with (at least) the hypochlorite salt. But with regard to the acid selected, it could include the monobasic lactic acid ($pK_a$ 3.86) up through the tribasic phosphoric acid ($pK_{a2}$=7.1), with other acids including, but not limited to acetic, tartaric, citric, succinic, adipic, and malic acid. In a preferred embodiment citric acid, a well-recognized acidulent, performs well. Those skilled in the relevant art may wish to consider another acidulent, as long it will achieve, in combination with the buffer-producing alkaline salt, the desired final pH in the oxychlorine system (preferably from about 5.5 to about 8.0).

The nature and amount of buffer-producing salt to be used would depend, in some respect, on the nature of the salt selected as well as the nature of the acidifying agent. In general, it should be one that creates a sufficiently alkaline pH (preferably ≧pH 11) at the concentration chosen to ensure continued stability of the co-dissolved sodium hypochlorite. When it is desired to also include sodium chlorite in the concentrate, when a two-part injection activation sequence is preferred, it is more important that the pH of the combined oxychlorine/buffer-producing salt lie significantly above pH 11. This is because the $pK_a$ of hypochlorous acid is about 7.5, and even at pH 11 there is sufficient $H^+$ ion in solution for enough HOCl to exist in an NaOCl solution that an undesired reaction with the chlorite anion could occur when such solutions are stored for prolonged times or higher temperatures.

In general, the solutions required for a three-step injection process will tend to have a greater long-term stability than those for a two-step activation process. There are fewer available, physiologically compatible buffer-producing salts that are applicable for this invention. While sodium carbonate is the salt comprising the preferred embodiment, trisodium phosphate is also applicable, although the selection is not necessarily limited to these choices. The important requirement is that the buffer-producing salt, at the concentration selected, is capable of reacting with the selected acidifying agent, at the concentration chosen, that the resulting system pH is physiologically compatible, and does not have a significant impact, upon reaction, with the tonicity of the final system. Those skilled in the art of buffer systems should be capable of such selections to achieve the desired end.

In a preferred embodiment, the physiological saline solution containing the $ClO_2$-containing oxychlorine composition can be prepared in a thickened, i.e., more viscous form, using one or more of a variety of physiologically-compatible thickeners, the identities of which are known to those skilled in the relevant art. For example there are a series of cellulose-ether thickeners which form thickened clear aqueous solutions, and which are of sufficient stability in the presence of an oxidant such as $ClO_2$ to resistant degradation for a sufficient time period during which the solution would be used.

Examples of such thickeners include, but are not limited to, xanthan gum, methylcellulose, hydroxyethylcellulose, methylhydroxypropylcellulose, and methylhydroxyethylcellulose.

A preferred viscosity range for these thickened isotonic saline solutions is from about 50 cps to about 2,500 cps. Obviously different concentrations of the respective thickening agents will be required to achieve the prescribed viscosity range. In all cases, the agents must yield a sufficiently clear solution to allow the $ClO_2$ concentration in the formulation to be determined spectrophotometrically. It should be noted that the reported $Cl_2O_4^-$ complex has an absorbance at the peak 360 nM absorption of $ClO_2$ that is relatively similar to that of $ClO_2$, so there will be probably small impact on the calculated concentration of $ClO_2$ on the basis of the measured Absorbance at that wavelength. Different viscosity compositions might be preferred in certain surgical intervention sites, such as in spinal laminectomies, where even more viscous gels may serve best.

The advantage of a thickened saline, from which to prepare the $ClO_2$-containing oxychlorine saline, is that the more viscous solution will tend to remain in situ, with less tendency to be diluted by physiological fluids, and thus be capable of delivering its protective effects for a longer period than the less-viscous solution, where the protective effects are a combination of adhesion-formation suppression and antisepsis of the exposed body site. When such a solution is prepared, for example, the thickener powder may be generally predispersed in a small quantity of an inert glycol (e.g., propylene glycol) and then the saline is slowly added to it, with stirring, until the saline become totally clear. Thereafter the thickened saline is used in the same manner as the Normal saline mentioned above i.e., addition of chlorite salt concomitant with, or followed by the hypochlorite/alkaline buffering salt solution, and then the acidifying solution. Of course, when such enhanced-viscosity saline formulations are preferred, such saline compositions are not generally available in medical facilities, and even more generally do not exist in isotonic, sterile form, whether in dispensing bags or bottles. Therefore such enhanced-viscosity isotonic saline solutions must be prepared beforehand, and stored (and suitably preserved) until time for use in the inventive method. It should be noted, however, that the oxychlorine formulations being described in this inventive method are highly microbiocidal, so that any microbial contaminant introduced by the thickening material and/or during preparation will, in all likelihood, be rapidly destroyed. In support of that projection, it is herein noted that there was no evidence, in the studies described in Examples 3 and 4, of contamination of the thickening agent, which certainly would have had negative effects in triggering of fibrous adhesion formation.

The inventive method and disclosed compositions can be effective in a broad range of post-surgical and adverse physiological situations, where the stimulation of fibroplasia leads to unwanted adhesions and scar formation. This applies to both internal intervention procedures and topical situations. As an example, following the use of the inventive method and composition as a post-surgical flush of the abdominal cavity, the sutured areas of the skin, during and after closure, can be irrigated with the same $ClO_2$/saline solution, to reduce the tendency for scar tissue to be formed on the skin. Such examples of the inventive disclosure are presented to illustrate and explain the present invention and should not be taken as limiting in any regard.

EXAMPLES

The following examples are presented to further illustrate and explain the present invention and should not be taken as limiting in any regard. It is anticipated that this inventive method will be applicable to at least the ten types of adhesions itemized in the Background section of this application, as well as other surgical intervention and pathological conditions, internal or topical, that inflict mammalian species. Unless otherwise indicated, all parts and percentages are by weight, and are given for the particular processing step described.

Example 1

This example illustrates the varying yields of chlorine dioxide which are obtained when different relative amounts of hypochlorous acid (from $OCl^-$) and chlorite ($ClO_2^-$) are combined. The comparative study involved the sequential addition, to 500 ml of 0.9% saline solution, of a sodium chlorite concentrate (A), a hypochlorite/carbonate concentrate (B), and a citric acid concentrate (C). For simplicity of calculation in the table, all concentrations expressed therein assume the same final 500 ml volume, which at most introduces a ~2% error in the calculations. The individual columns in the table are self-explanatory, with the additional clarifications:

The $ClO_2$ that is formed is expressed as both parts per million (mg/liter) and mg//½ liter in the adjoining column.

The sodium chlorite concentrations in the solutions are shown as initially prepared, both as the whole salt and as the chlorite ion component in the adjoining column. The Residual chlorite, that is the amount of chlorite remaining in solution following the reaction (assuming minimum transformation to chloride and chlorate ions) has been presented in two ways: The upper values, in lighter text, are the amounts of chlorite calculated to be present on the basis of the difference between the initial chlorite levels and the $ClO_2$ formed (shown as both mg/500 ml and ppm). This assumes that the only reaction mechanism is the following: $HOCl+2ClO_2^- \rightarrow 2ClO_2+Cl^-+OH^-$. The lower values, in boldface, are the actual levels of chlorite determined by micro-iodometric analysis, which involved the initial aeration of the mixed solution, to eliminate the $ClO_2$ gas (both color and odor), followed by titration of the chlorite. In the case of run δ, where there was an excess of hypochlorite, aeration did not eliminate the chlorine-like odor, indicating the absence of residual chlorite from the surfeit of hypochlorous acid. The residual chlorite level is therefore marked NA (not analyzed). The "calculated" residual chlorite level was not applicable, in the excess of hypochlorite, where presumably the reaction $HOCl+ClO_2^-+OH^- \rightarrow ClO_3^-+Cl^-+H_2O$ played a significant role, which is consistent with the lower yield of $ClO_2$ (40 ppm) than for run β, where the same initial level of chlorite yielded higher 52.4 ppm of $ClO_2$.

The lower levels of chlorite actually found are presumably a result of the competitive analysis which occurs transiently at a higher pH above about pH=6 upon acidification prior to the conversion effected by the above equation: $HOCl+ClO_2^-+OH^- \rightarrow ClO_3^-+Cl^-+H_2O$. In this case the efficiency of conversion is reduced by conversion to chlorate and chlorate, and lesser formation of $ClO_2$.

"Conversion efficiency" is a measure of the percentage of $ClO_2$ formed in comparison to the amount of $ClO_2^-$ added to the solution, based on the direct oxidation of chlorite to $ClO_2$, where is the predominating reaction. It is thus a % of total theoretical yield of $ClO_2$.

"Volume ratio" represents the ratio between the solution volumes of the B and A solutions, i.e., the hypochlorite/carbonate solutions and the chlorite solutions.

The "$HOCl/ClO_2^-$ adequacy %" is a measure of the availability of sufficient HOCl (as formed from NaOCl) to fully oxidize the chlorite ion to $ClO_2$, according to the above equation. When there is less than sufficient HOCl (i.e., an excess of $ClO_2^-$) for complete oxidation, the adequacy will be <100%. This is true for 3 of the 4 runs in this study. When there is an excess of HOCl, the ratio will be >100%, as in run γ.

The solution pH represents the capacity of the bicarbonate/carbonate buffer to achieve a solution pH compatible with physiological solutions, generally acknowledged to be in the range of about 5.5 to about 8.0 for brief tissue contact.

Example 1

OXYCHLORINE GENERATION STUDIES WITH VARYING CHLORITE, ACID, AND HYPOCHLORITE LEVELS

| | VOLUME (ml)* | | | $ClO_2$ formed | | Sodium Chlorite (pure basis) | | | | | Volume Ratio | HOCl/$ClO_2^-$ Adequacy | Sol'n |
| | | | | | | Initial as $ClO_2^-$ | Residual as $ClO_2^-$ | | | | Conversion Efficiency | | |
| | Order of Addition | | | | | | Calculated | | Analysis | | | | |
| RUN | A | B | C | ppm | mg/500 ml | mg/500 ml | | | ppm | | B/A | % | pH |
| α | 1 | 5 | 5 | 111.8 | 55.9 | 134  99.9 | 44 | 16.3 | 88 | 32.5 | 56.0% | 5:1 | 72.7 | 5.76 |
| β | 0.5 | 2.5 | 2.5 | 52.4 | 26.2 | 67  50.0 | 23.8 | 16.4 | 48 | 32.8 | 52.4% | 5:1 | 72.7 | 6.00 |
| γ | 1 | 2.5 | 2.5 | 60.1 | 30.0 | 134  99.9 | 69.9 | 64.5 | 140 | 129 | 30.0% | 2½:1 | 36.4 | 6.35 |
| δ | 0.5 | 5 | 5 | 40.0 | 20.0 | 67  50.0 | (27.0) | **NA\*\*** | (54.0) | **NA\*\*** | 59.7% | 10:1 | 145.4 | 5.54 |

*per 500 ml of saline

**NA-not analyzed: The solution's chlorine-like odor, from both $ClO_2$ and hypochlorite, could not be dispelled by aeration, as in the other samples. There is little likelihood of residual chlorite with excess hypochlorite present.

A = Sodium chlorite; 134 mg/ml of water (pure basis)

B = 0.60% sodium hypochlorite/0.60% sodium carbonate.

C = 2.0% citric acid solution.

In this example, it can be seen that the least efficient conversion to $ClO_2$ occurs in run γ where there is insufficiently-formed hypochlorous acid for the complete oxidation of the chlorite ion present. In the runs α and β, there is an excess of chlorite ion, some of which is unconsumed, and remains as an excess. As noted before, in run γ, there is an excess of hypochlorite with respect to the chlorite. It can be also noted that even with half the amount of carbonate buffer in run γ, as cf. the other runs, there it is still adequate to maintain the final pH at an acceptable physiological level [pH 6.35]. Of further note is that the $ClO_2:ClO_2^-$ molar ratios in runs α, β and γ, respectively, are 3.40, 1.60, and 0.47.

Example 2

This example illustrates the application of the inventive method, using two activating solutions, as opposed to the three that were evaluated in range-finding study in Example 1. In the latter study, different ratios of the hypochlorite/carbonate solution to the chlorite solution were investigated, to select those concentrations more favorable to combine into a mixed chlorite/hypochlorite/carbonate solution. This mixed solution was then added to a physiological saline solution [0.9% NaCl] in a predetermined volume, and an equal volume of a citric acid solution was then Example 2

OXYCHLORINE GENERATION STUDIES USING TWO-PART ACTIVATOR; OXYCHLORINE (OX) AND CITRIC ACID (CA) MIX

| | | | | | Sodium Chlorite (pure basis) | | | | | |
|---|---|---|---|---|---|---|---|---|---|---|
| | VOLUME (ml) | | $ClO_2$ formed | | Initial as $ClO_2^-$ | Residual $ClO_2^-$ By analysis | | $ClO_2:ClO_2^-$ Molar | Volume Ratio Sol'n | |
| RUN | OX | CA | ppm | mg/500 ml | mg/500 ml | | ppm | Ratio | OX/CA | pH |
| I | 5.0 | 5.0 | 112.4 | 56.2 | 134 | 99.9 | 21.7 | 43.4 | 3.44 | 1:1 | 5.76 |
| II | 2.5 | 2.5 | 52.1 | 26.1 | 67 | 50.0 | 32.3 | 64.7 | 0.81 | 1:1 | 6.00 |
| III | 2.5 | 2.5 | 57.7 | 28.9 | 67 | 50.0 | 31.1 | 62.2 | 0.93 | 1:1 | 6.35 | added to convert the hypochlorite to hypochlorous acid. Two identical solutions (i.e., same concentrations of all ingredients) were evaluated, with the only difference being the uniformity of acidification. As has been shown in the body of this disclosure, there is a reaction between hypochlorite and chlorite which minimizes $ClO_2$ formation in favor of chlorate and chloride ions, i.e., $HOCl+ClO_2^-+OH^- \rightarrow ClO_3^-+Cl^-+H_2O$. In the controlled addition (Run III below), the saline/oxychlorine composition was stirred while the acid was being introduced, in an attempt to lower the pH quickly and uniformly throughout the solution, to the acidic side, and minimize the availability of OH' to contribute to the side, non-productive reaction.

Concentrations and volumes of components (in order of combination):

Aqueous saline, 0.9%: Volume 490 ml.

Oxychlorine concentrate: $NaClO_2$—2.68%; NaOCl—0.60%; $Na_2CO_3$—0.60% (pH 11.08)

Run I: Volume 5 ml Run II: Volume 2.5 ml Run III: Volume 2.5 ml

Citric Acid concentrate: 2.0%

Run I: Volume 5 ml Run II: Volume 2.5 ml Run III: Volume 2.5 ml

The data demonstrate the utility of the two-part activating system, comprised of mixed chlorite and hypochlorite species+carbonate salt, in one part, and the activating acid in the other part. The data from Runs II and III confirm the projection that the greater the uniformity of acidification of the saline/oxychlorine composition, the more efficient the conversion to chlorine dioxide rather than other anions. In all cases it should be again noted that the $ClO_2:ClO_2^-$ molar ratios in all three runs are significantly below the minimum of $\geq 5:1$, as taught in the '725 patent noted earlier. All solutions, following formation, have physiologically-compatible pH values, in the isotonic system.

Example 3

This example is provided to demonstrate the marked effect of the $ClO_2$-oxychlorine systems on the formation of post-surgical adhesions in a group of mammalian species. The treatment solutions, unthickened and thickened, were prepared using the sequential three-solution injection system into sterile saline solution. The solution ratios paralleled that shown in Example 1, run α. Abdominal adhesions were produced in three groups of male Wistar rats (200-230 g, 10 weeks old, feed with Purina chow and water ad libitum, subjected to light-dark cycles of 12×12 h) following the model reported by Buckenmaier et al. There were five animals per each of the three groups. In brief: the animals were anesthetized (pentobarbital 45 mg/kg, intraperitoneal, i.p.), the lower abdominal area was shaved, washed and cleaned with povidone iodine. A laparotomy was done through a midline incision. The parietal wall of the peritoneum was exposed and four vessels were located (the distances between the vessels was at least 1 cm). This provided 20 (4×5) sites in each group of the control or two Test animals. Their vessels were ligated with 3-0 silk to produce ischemia. The peritoneum around the suture was gently abraded with the tip of scissors. The laparotomy incision was then closed in two layers. The peritoneum and abdominal muscles were closed with continuous 3-0 prolene and then the skin was closed with continuous 3-0 dermalon.

Before the peritoneum was completely closed, the treatment or control solutions were infused into the peritoneal cavity, either 10 cc of isotonic saline solution (control), or the same volume of an unthickened $ClO_2$ sterile saline solution, or one that had been initially thickened with 0.6% Natrosol MR (a hydroxyethylcellulose ether) prior to activation to form a $ClO_2$ solution.

An adhesion score was calculated by ascribing one point to each adhesion formed at each ischemic button. Additionally, two points were given if there was any adhesion to the liver, between portions of the gut, or to the peritoneal wound.

Results:

The adhesion severity scores, as described above, clearly show the efficacy of the treatments, as follows:

| Treatment | Rat Number | Score |
|---|---|---|
| Isotonic saline solution | 1 | 2 |
| | 2 | 2 |

-continued

| Treatment | Rat Number | Score |
|---|---|---|
| | 3 | 5 |
| | 4 | 6 |
| | 5 | 2 |
| | | Ave = 3.4 |
| Unthickened saline solution (ClO$_2$, 96 ppm) | 6 | 0 |
| | 7 | 0 |
| | 8 | 3 |
| | 9 | 1 |
| | 10 | 1 |
| | | Ave = 1.0 |
| Thickened saline solution (ClO$_2$, 89 ppm) | 11 | 0 |
| | 12 | 0 |
| | 13 | 0 |
| | 14 | 0 |
| | 15 | 0 |
| | | Ave = 0 |

The group treated with only isotonic saline solution is significantly different (p<0.05) from the other two groups. The groups treated with the unthickened and the thickened ClO$_2$ oxychlorine-solutions are statistically similar (p>0.05) as evaluated by the One-way Anova (Prism 5 program).

Conclusion: both ClO$_2$ containing-oxychlorine solutions significantly reduced adhesion formation. The treatment by a solution of increased viscosity, intended to maintain solution contact, was of apparent value.

A tabulation of these data in FIG. 1 shows the differences quite remarkably.

Example 4

This example shows the effects on adhesion formation using lower ClO$_2$-containing oxychlorine compositions than used in Example 3. The procedures and animals were the same as used in Example 3. However the concentrations of the thickened and unthickened ClO$_2$ solutions were reduced (40 and 74 ppm, respectively).

Results:

| Treatment | Rat Number | Score |
|---|---|---|
| Isotonic saline solution | 16 | 2 |
| | 17 | 4 |
| | 18 | 4 |
| | 19 | 1 |
| | 20 | 4 |
| | | Ave. = 3.0 |
| Unthickened saline solution (ClO$_2$, 74 ppm) | 21 | 0 |
| | 22 | 2 |
| | 23 | 1 |
| | 24 | 0 |
| | 25 | 0 |
| | | Ave. = 0.6 |
| Thickened saline solution (ClO$_2$, 40 ppm) | 26 | 0 |
| | 27 | 0 |
| | 28 | 1 |
| | 29 | 0 |
| | 30 | 1 |
| | | Ave. = 0.4 |

The group treated with isotonic saline solution is significantly different (p<0.05) from the other two groups. The groups treated with the unthickened and the thickened ClO$_2$-containing oxychlorine solutions are statistically similar (p>0.05), although such a comparison ignores the fact that the solution with almost half the ClO$_2$ concentration has a better score than that of the higher concentration. Statistics were again determined using One way Anova (Prism 5 program).

Conclusion: both ClO$_2$ solutions significantly reduced adhesion formation, where enhanced viscosity played an apparently positive role.

Figure 2:
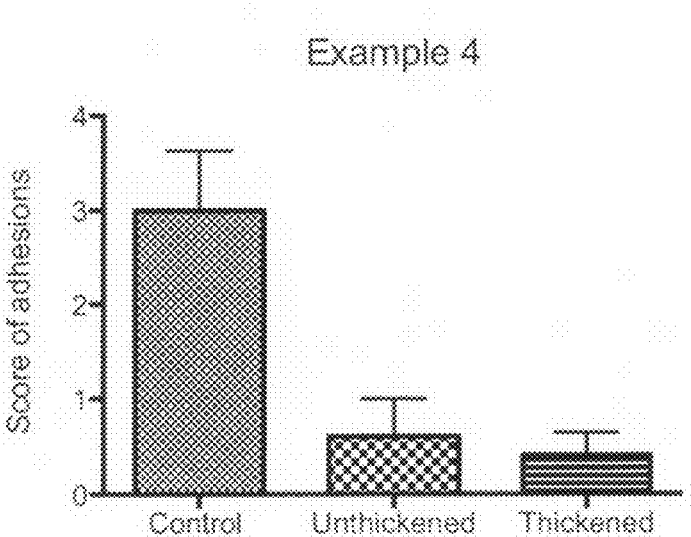
FIG. 2 is a bar graph of adhesion severity scores in Example 4 for thickened and unthickened $ClO_2$ oxychlorine-saline solutions and control saline solution. The $ClO_2$ oxychlorine concentrations were lower in Example 4 relative to Example 3.

The corresponding bar graph of these data in FIG. 2 shows the differences quite vividly.

Example 5

This example illustrates the combined effect of the antimicrobial and adhesion-suppressing activity of the inventive compositions in treating infections and preventing their effect on adhesion formation. It is quite common to have surgical patients with abdominal cavity infections (e.g., a trauma with associated bowel perforation, appendicitis from a burst appendix). Fecal or bacterial contamination of the abdominal cavity increases the inflammatory factors that contribute to adhesion formation. Since the ClO$_2$-oxychlorine compositions are antiseptic and, as seen in Examples 3 and 4, inhibit the formation of post-surgical adhesions, the inventors chose to modify a well-known ("Buckenmaier") adhesion model in order to gauge the suppression of their further formation as a result of the fecal contamination's provocation of the inflammatory reaction in the abdominal cavity. One hour before the surgical procedure (as in Example 3), the animals received intraperitioneal infusions of their own feces diluted in isotonic saline solution (50 mg/Kg, diluted in 400 µl). In this protocol the treatments were: isotonic saline solution and an unthickened 110 ppm ClO$_2$-containing oxychlorine isotonic saline composition.

Results

| Treatment | Rat Number | Score |
|---|---|---|
| Isotonic saline solution | 31 | 8 |
| | 32 | 7 |
| | 33 | 10 |
| | 34 | 7 |
| | 35 | 5 |
| | 36 | 7 |
| | 37 | 6 |
| | | Ave = 7.1 |
| Unthickened solution (ClO$_2$, 110 ppm) | 38 | 5 |
| | 39 | 2 |
| | 40 | 2 |
| | 41 | 1 |
| | 42 | 0 |
| | 43 | 1 |
| | | Ave. = 1.8 |

The group treated with isotonic saline solution is significantly different (p<0.001) from the group treated with the unthickened ClO$_2$ oxychlorine-saline solution. Unpaired "t" test (Prism 5 program).

Conclusion: the ClO$_2$-oxychlorine saline solution significantly reduced enhanced adhesion formation triggered by the infused bacterial contaminants. Indeed, the fecal contamination increased the average of adhesions to more than double (average of 7.1 with fecal contamination, compared to 3.4 and 3.1 in experiments 3 and 4). Even in these conditions the unthickened ClO$_2$ solution significantly reduced the number of adhesions.

Example 6

The mixed oxychlorine composition, shown in the Run δ formula in Example 1 can be used, in a thickened composition, for the topical prevention, inhibition and treatment of infections produced in surgical wounds with a high potential for infection (e.g., an emergency laparotomy after trauma, a topical wound infection after colonic surgery) or skin punctures (including battlefield injury) which include underlying damage to other structures, such as those produced by trauma, stabbing or gun-shot lesions. This composition is comprised of both $ClO_2$ and hypochlorite/hypochlorous acid, to both disinfect the wound and suppress scar tissue formation while the wound is healing.

A 500 ml portion of sterile saline, previously thickened by slow addition of 3.75 gm (yielding 0.75%) of xanthan gum to achieve uniformity, is serially injected with 1 ml of a solution containing 67 mg of sodium chlorite (pure basis), followed by 5 ml of a mixed concentrate comprised of 0.60% each of sodium hypochlorite and sodium carbonate. After the contents of the first two injections have been thoroughly mixed into the thickened isotonic saline, 5 ml of a 2% citric acid solution is injected, with the solution being rapidly introduced with continuous thorough mixing of the viscous composition. The mixture will rapidly become a light yellow-green in appearance, and a generous portion should be then applied to the person's affected area, covered by a gauze bandage. The gauze should be intermittently resaturated with the mixture, every 30 minutes for the next four-hour period. The unused portion of the composition should be refrigerated, and periodically reapplied thereafter, on an ad libitum basis, for the next two days.

Example 7

This example demonstrates the application of the multiple oxychlorine system disclosed in this inventive method to attenuate epidural fibrosis, to reduce spinal fibrosis as a result of spinal surgery. Rats are used as the initial validation model prior to application to human subjects. Sixty percent of lumbar spinal surgery patients, who undergo this procedure, suffer thereafter from so-called "Failed back surgery syndrome". This painful condition requires many to then undergo follow-up corrective surgery, with fibrosis being the cause of 25% of this "failed-back" syndrome. The inventive $ClO_2$-containing oxychlorine technology, by demonstrably inhibiting fibrotic tissue formation, could prove to be of definite value for application during spinal surgery. In this example a composition comprised of both $ClO_2$, at 75 ppm, and additional chlorite ($ClO_2^-$) ion, is prepared with 500 ml of sterile saline that has been pre-thickened with 3.75 gm of Natrosol MR. Upon achieving a uniform solution, the isotonic saline is then injected with 5.0 ml of a solution concentrate containing 0.40% sodium hypochlorite and 0.6% sodium carbonate, to which volume 90 mg of sodium chlorite (pure basis) has been added. Following uniform dispersion, the thickened alkaline composition is injected with 5.0 ml of a 2.0% citric acid solution, with continuous mixture so that the acid is quickly and uniformly distributed to quickly reduce the pH to below neutrality.

The animals, male Sprague Dawley rats (400 g), are divided in two groups (n=10 in each group): 1) Control and 2) treated with the gelled $ClO_2$ composition. Both groups are then subjected to laminectomy: Under ketamine/buprenorphine anesthesia, the animals' backs are washed, shaved and covered with povidone iodide. A midline incision is made along the spine in the lumbar region, from L4 to L7 to expose the laminae. Using a microscope, a right laminectomy is perfomed at L5 and L6, carefully exposing the dura. A small amount of bone is applied to prevent spontaneous closure of the laminectomy. The dura and the spinal nerve are gently retracted to the middle line to expose the L5-6 disc. A 27 gauge needle is inserted into the disc to create a disc injury. After hemostasis, a portion of the $ClO_2$ gel is expressed, through a syringe, into the area, and the wound is closed. Additional buprenorphine is administered to produce analgesia. Three weeks later the tissue is isolated and the damage is evaluated as described by Sabuncuoglu, with fibrosis evaluated by means of light microscopy. The tissues are fixed in neutral buffered formaldehyde for two days, then decalcified in De Castro's fluid, dehydrated in alcohol and embedded in paraffin. The tissue is cut into 4-6 μm slides and stained with hematoxylin, eosin and Masson's trichrome stains. The sections are evaluated for fibroblasts numbers, adhesion degree between dura mater and fibrous tissue and new bone formation in the laminectomy region. The positive results will then support the use of this inventive composition in human subjects.

While various embodiments of the present invention have been shown and described, it would be understood by one skilled in the art that the invention is not limited thereto and that further modifications, changes or additions can be made without varying from the scope of the invention.

REFERENCES

| 6,284,152 | September 2001 | Kross | 252/187.21 |
| 5,820,822 | October 1998 | Kross | 422/37 |
| 5,622,725 | April 1997 | Kross | 424/665 |
| 4,507,285 | March 1985 | Kuhne, et al | 424/615 |

Buckenmaier, C. C. et al., Comparison of antiadhesive treatments using an objective rat model. Am Surg 1999; 65:274-282.

Reed, et al,. A neurokinin 1 receptor antagonist decreases postoperative peritoneal adhesion formation and increases peritoneal fibrinolytic activity Proc. Nat'l Acad. Sci. vol. 101, no. 24, 9115-9120, Jun. 15, 2004

Reed, et al., Journal of Surgical Research 108, 165-172 (2002)

Kenyon, A. J et al., "Controlled wound repair in guinea pigs, using antimicrobials that alter fibroplasia" in Am J Vet Res. 47 (1):96-101 (1986).

Gordon, Gilbert et al., The Chemistry of Chlorine Dioxide, Prog. Inorg. Chem. 15:201, pp. 234-286, (1972).

Gordon, Gilbert and Emmenegger, Complex Ion Formation between $ClO_2$ and $ClO_2^-$, Inorg. Nucl. Chem. Letter Vol. 2, 1966, Pergamon Press Ltd. (1966).

Masschelein, W. J., "Chlorine Dioxide; Chemistry and Environmental Impact of Oxychlorine Compounds. P. 57, Ann Arbor Science publishers, (1979).

Körtvélyesi, Zsolt, "Analytical Methods for the Measurement of Chlorine Dioxide and Related Oxychlorine Species in Aqueous Solution" thesis for Doctor of Philosophy, Miami University, Chemistry, 2004.

Schier, F., Tetrachlorodecaoxide does not jeopardize anastomotic healing: an experimental study in animals, Ped. Surg. Intnl, (17), No. 2-3, March (2001)

Robson, M. C. et al., Hypochlorous Acid as a Potential Wound Care Agent, Part II; J. Burns and Wounds, Vol. 6, p. 80-90, (2007).

Encyclopaedia Britannica; website url: britannica.com/EBchecked/topic/150035/Dakins-solution Turna B, Aron M, Frota R, Desal M M, Kaouk J, Gill I S. Feasibility of laparoscopic partial nephrectomy after previous ipsilateral renal procedures. Urology 2008; 72:584-588.

Cooper R G, Mitchell W S, Illingworth K J, et al., The role of epidural fibrosis and defective fibrinolysis in the persistence of postlaminectomy back pain. Spine 1991; 16:1044-48.

Kulkarni A V, Massie J B, Zauner F, Murphy M, Akeson W H. Novel biomechanical quantification methodology for lumbar intraforaminal spinal nerve adhesion in laminectomy in disc injury rat model. J Neurosci Methods 2007; 166:20-23.

Sabuncuoglu H, Bavbek M, Sabuncuoglu B, Gadelha E, Köse K, Preul M. Attenuation of postlaminectomy epidural fibrosis with monoclonal antibodies against intercellular adhesion molecule—1 and CD-18. Spine J 2007;7:459-465.

Ward, B. C., and Panitch, A. Abdominal Adhesions: Current and Novel Therapies. *J Surg Res,* 2009, in press.

We claim:

1. A composition prepared on-site for the suppression or reduction in the likelihood of formation of fibrous adhesions in tissue of a mammal comprising:
   an isotonic saline solution and
   aqueous concentrates which are sequentially injected into the isotonic saline solution immediately prior to use comprising 1) a chlorite salt, 2) a hypochlorite salt combined with a physiological buffer-producing salt of a multibasic acid, and 3) an acidifying agent, to provide the composition with a molar ratio of formed chlorine dioxide to residual chlorite ion equal to or less than about 3.5 to 1, the level of chlorine dioxide in the composition being in the range from about 10 parts per million (ppm) to about 110 ppm.

2. The composition of claim 1 wherein the acidifying agent has a $pK_a$ value that lies in the range of about 3.8 to about 7.1.

3. The composition of claim 1 wherein the acidifying agent is selected from the group consisting of lactic acid, phosphoric acid, acetic acid, tartaric acid, citric acid, succinic acid, adipic acid, malic acid and combinations thereof.

4. The composition of claim 1 wherein the acidifying agent is citric acid.

5. The composition of claim 1 wherein the physiological buffer-producing salt of a multibasic acid is selected from the group consisting of sodium carbonate, trisodium phosphate, and combinations thereof.

6. The composition of claim 1 wherein the physiological buffer-producing salt is sodium carbonate.

7. The composition of claim 1 wherein the chlorite salt is sodium chlorite and the hypochlorite salt is sodium hypochlorite.

8. The composition of claim 1 further comprising a thickening agent.

9. The composition of claim 8 wherein the thickening agent is selected from the group consisting of xanthan gum, methylcellulose, hydroxyethylcellulose, methylhydroxypropylcellulose, methylhydroxyethylcellulose and combinations thereof.

10. The composition of claim 1 wherein a molar ratio of the hypochlorite salt with respect to the chlorite salt provides about a 10% to about a 50% molar excess with respect to an amount required for oxidation of the chlorite to chlorine dioxide.

11. The composition of claim 10 wherein the about 10% to about 50% molar excess corresponds to about 18 mg per liter to about 25 mg per liter, for compositions that have about 10 ppm of chlorine dioxide, to about 200 to about 270 mg per liter for composition that have about 110 ppm of chlorine dioxide.

12. A method for suppressing or reducing the likelihood of the development of fibrous adhesions in tissue of a mammal comprising treating the tissue with an effective amount of a composition prepared on-site comprising a multiple oxychlorine species-containing buffered, isotonic composition, further comprising providing an isotonic saline solution and sequentially injecting into the isotonic saline solution aqueous concentrates of 1) a chlorite salt, 2) a hypochlorite salt combined with a physiological buffer-producinq salt of a multibasic acid, and 3) an acidifying agent.

13. The method of claim 12 wherein the chlorite salt and the hypochlorite salt combined with the physiological buffer-producing salt of the multibasic acid are contained in one concentrate, which is first injected into the isotonic saline solution followed by injection of the acidifying agent.

14. The method of claim 12 wherein the acidifying agent has a $pK_a$ value that lies in the range of about 3.8 to about 7.1.

15. The method of claim 12 wherein the acidifying agent is selected from the group consisting of lactic acid, phosphoric acid, acetic acid, tartaric acid, citric acid, succinic acid, adipic acid, malic acid and combinations thereof.

16. The method of claim 12 wherein the acidifying agent is citric acid.

17. The method of claim 12 wherein the physiological buffer-producing salt of a multibasic acid is selected from the group consisting of sodium carbonate, trisodium phosphate, and combinations thereof.

18. The method of claim 12 wherein the physiological buffer-producing salt is sodium carbonate.

19. The method of claim 12 further comprising injecting the acidifying agent at a rate such that the pH of the alkaline system drops rapidly to below a pH of about 6.4 but significantly above a pH of about 3.5, thereby optimizing the conversion of chlorite ion to chlorine dioxide and minimizing creation of undesired chlorine-containing end products.

20. The method of claim 12 further comprising increasing a viscosity of the standard saline solution prior to the injecting steps.

21. The method of claim 20 wherein the viscosity is increased to a range of from about 50cps to about 2,500 cps.

22. The method of claim 20 further comprising increasing the viscosity of the saline solution by adding a thickening agent thereto selected from the group consisting of xanthan gum, methylcellulose, hydroxyethylcellulose, methylhydroxypropylcellulose, methylhydroxyethylcellulose and combinations thereof.

23. The method of claim 12 wherein the treating of the tissue comprises perfusing a surface wound to suppress scar and keloid formation.

24. The method of claim 12 wherein the treating of the tissue comprises bathing ocular surfaces.

25. The method of claim 12 wherein the treating of the tissue comprises applying the composition to suppress or prevent symblepharon, the adhesions between palpebral conjunctivae of the eyelid and bulbar conjunctivae of the eye ball or following a pneumothorax to suppress pleural adhesion formation, or to suppress intrauterine synechiae produced by a myomectomy or mechanical abortion.

26. The method of claim 12 wherein the treating of the tissue comprises applying the composition during optic surgery.

27. A method for suppressing or reducing the likelihood of the development of fibrous adhesions resulting from a surgical procedure performed on a surgical site comprising treating the surgical site with an effective amount of a composition prepared on site comprising a multiple oxychlorine species-buffered, isotonic composition further comprising, immediately prior to use of the composition, making the composition by providing an isotonic saline solution and sequentially injecting into the isotonic saline solution aqueous concentrates of 1)a chlorite salt, 2) a hypochlorite salt combined with a physiological buffer-producing salt of a multibasic acid, and 3) an acidifying agent, to provide a composition having a molar ratio of formed chlorine dioxide to residual chlorite ion equal to or less than about 3.5to 1, the level of chlorine dioxide being in the range from about 10parts per million (ppm) to about 110 ppm.

28. The method of claim 27 further comprising adding a thickening agent to provide the composition with a viscosity of from about 50 cps to about 2,500 cps to prolong retention at the surgical site.

29. The method of claim 27 wherein the surgical site is a topical site and treating the surgical site comprises perfusing the topical site.

30. The method of claim 27 wherein the surgical procedure involves an incision of the peritoneal cavity for correction of pathological conditions including, but not limited, to corrective surgery, puncture and tear wounds, burst appendices, for suppressing or eliminating formation of post-surgical internal fibrous adhesions.

31. The method of claim 27 wherein the surgical procedure is undertaken to correct pre-existing adhesions, by severing the adhesion to create a surgical site and treating the surgical site to suppress reformation.

* * * * *